United States Patent [19]

Hallgren et al.

[11] 4,360,477

[45] Nov. 23, 1982

[54] CARBONYLATION OF ALKANOLS

[75] Inventors: John E. Hallgren; Gary M. Lucas, both of Scotia, N.Y.

[73] Assignee: General Electric Company, Schenectady, N.Y.

[21] Appl. No.: 319,509

[22] Filed: Nov. 9, 1981

[51] Int. Cl.³ .............................................. C07C 68/00
[52] U.S. Cl. .................................................... 260/463
[58] Field of Search ......................................... 260/463

[56] References Cited

U.S. PATENT DOCUMENTS

| | | | |
|---|---|---|---|
| 3,114,762 | 12/1963 | Mador et al. | 260/463 |
| 3,227,740 | 1/1966 | Fenton | 260/463 |
| 3,846,468 | 11/1974 | Perrotti et al. | 260/463 |
| 3,952,045 | 4/1976 | Gaenzler et al. | 260/463 |
| 3,980,690 | 9/1976 | Cipriani et al. | 260/463 |
| 4,131,521 | 12/1978 | Cipris et al. | 204/59 |
| 4,218,391 | 8/1980 | Romano et al. | 260/463 |

FOREIGN PATENT DOCUMENTS 45-11129  4/1970  Japan ................................. 260/463

Primary Examiner—Donald G. Daus
Assistant Examiner—M. C. Eakin
Attorney, Agent, or Firm—Joseph T. Cohen; James C. Davis, Jr.

[57] ABSTRACT

Alkanols can be carbonylated with carbon monoxide and oxygen at elevated temperatures in the presence of certain copper salts to form dialkyl carbonates. The invention also covers the carbonylation by recycling of the azeotropic mixture of methanol and the corresponding dimethyl carbonate.

9 Claims, No Drawings

CARBONYLATION OF ALKANOLS

FIELD OF THE INVENTION

The field of polycarbonates resins is well known. The production of such materials for the formation of fibers and shaped bodies is well developed. However, generally these materials have been formed by the interaction of phosgene with one of a number of dihydroxy organic materials required to form the polycarbonate. The art has long sought a way to avoid the use of phosgene for environmental and toxic reasons.

While the use of an alkylcarbonate in the reaction, in place of phosgene, has been suggested, truly economical ways to produce the alkyl carbonate have not to my knowledge been shown in the prior art. This is true notwithstanding a large number of patents which have dealt with the production of such alkyl carbonates by a variety of processes. Merely as examples, U.S. Pat. No. 3,114,762 Mador et al has taught the reaction of an aliphatic alcohol with carbon monoxide in the presence of a platinum or palladium catalyst to produce a dialkyl carbonate. It was necessary to include copper salts in this mixture in order to reoxidize the platinum or palladium catalyst. Obviously, such a process was not economical in view of the cost of the platinum or palladium catalyst. A mercuric salt in an organic solvent was employed in the production of dialkyl carbonates by the reaction of alcohols with carbon monoxide in U.S. Pat. No. 3,227,740—Fenton. However, stoichiometric quantities of the mercuric salt were required and the toxic qualities of the mercuric salt presented problems.

Similarly, in Perrotti et al., U.S. Pat. No. 3,846,468, carbonic acid esters were prepared by the reaction of an alcohol and carbon monoxide and oxygen in the presence of a complex copper catalyst. Stoichiometric quantities of the copper were, again, required and, in addition, the presence of an amine, nitrile, or phosphine was necessary.

In Cipriani et al., U.S. Pat. No. 3,980,690, the carboxylation of an alcohol into the corresponding carbonate by reaction of the alcohol with oxygen and carbon monoxide is taught. Here, a stoichiometric quantity of a copper salt is employed, the copper salt being immobilized by a polymer bound amine. Catalytic quantities of copper are employed in Gaenzler et al., U.S. Pat. No. 3,952,045, but a Lewis acid must be employed, simultaneously. Cipris et al., U.S. Pat. No. 4,131,521, show the electrochemical production of alkyl carbonates employing a halide-containing electrolyte and a paraffinic monohydric or 1,2-dihydric alcohol, under a carbon monoxide atmosphere.

In short, so far as is known, none of the processes described by the prior art has provided an economical process for producing alkyl carbonates which might be used in place of phosgene for the production of polycarbonate resins.

BRIEF DESCRIPTION OF THE INVENTION

In accordance with the present invention, particularly in view of the prior art, it has unexpectedly been discovered that alkyl carbonates can be produced from alkanols, in the presence of carbon monoxide and oxygen, at elevated pressures and temperatures, employing a copper catalyst, e.g., a cupric halide catalyst, in small catalytic amounts, without the necessity of complexing the copper catalyst. By the utilization of such a system, it is possible to recycle the catalyst system, since the catalyst is not water sensitive. Previously described systems have not allowed for this recycle, because the catalyst systems have been water-sensitive. Additionally, many of the previous systems, as indicated above, have required not catalytic quantities of the copper material, but stoichiometric quantities.

Because the present catalyst system is not sensitive to the water coproduced in the reaction, it is not necessary to remove the water during the reaction process, thus resulting in a simpler, more economical, more facile reaction. The reaction according to the present invention, is carried out at temperatures above 170° C., e.g., to as high at 350° C., preferably 180° to 250° C., and at elevated pressures, e.g., from 600 to 1,500 psi or higher if desired. When using methanol, one produces two azeotropes, one of dimethyl carbonate and water, boiling at about 77° C., and a second of methanol and dimethyl carbonate boiling at about 63° C. It has been found that the present invention can be carried out employing, as a feed or recycle, an essentially azeotropic mixture of the methanol and dimethyl carbonate resulting in a desirable 20% conversion to dimethyl carbonate in the first reaction of the methanol and CO, while recycling both the azeotrope and the catalyst employed, will produce additional amounts of dimethyl carbonate.

While small amounts of certain impurities, such as dimethyl formal and methyl formate are produced in the reaction, e.g., in the aforesaid Gaenzler et al patent, the amounts so produced are substantially less than with prior art processes employed to produce the dialkyl carbonates.

The amount of the copper catalyst material employed in the reaction in accordance with the present invention is in catalytic amounts. Generally the amount can be varied widely but on a weight basis, advantageously ranges from approximately 0.02% to 1.5%, based on the weight of the methanol. The time of reaction is generally over in less than two hours.

DESCRIPTION OF THE PREFERRED EMBODIMENTS

In accordance with the present invention, dialkylcarbonates are produced from alkanols in accordance with equations (I), below:

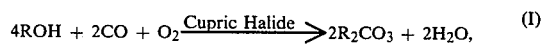

$$4ROH + 2CO + O_2 \xrightarrow{\text{Cupric Halide}} 2R_2CO_3 + 2H_2O, \quad (I)$$

where R is preferably $C_{1-4}$ alkyl selected from the class consisting of methyl, ethyl, propyl, isopropyl, and butyls.

The reaction is preferably carried out at a temperature of from 170° to 300° C. Preferably, from the standpoint of reaction rate and production of byproducts, the preferred reaction temperature is from 180° C. to 250° C. The reaction is carried out under pressure, generated by carbon monoxide and oxygen, e.g., from 600 to 1,500 psi or higher. The oxygen source may be in the form of gaseous oxygen or air. Oxygen gas is preferred.

The copper catalyst employed according to the present invention is a cupric halide, e.g., cupric chloride, cupric bromide, etc. The amount of catalyst employed will depend upon the rate of conversion to dialkyl carbonate and the avoidance of byproducts in the reaction mixture.

As indicated in equation (I), the normal reactants according to the present invention are alkanol, carbon monoxide, and oxygen. The dialkyl carbonate is recovered from the reaction mixture, and the copper catalyst is recovered from the water phase of that mixture. However, as previously indicated, two azeotropes are formed. When using methanol, these two azeotropes are a water-dimethyl carbonate azeotrope, comprising about 11% water and boiling at 77° C., and a methanol-dimethyl carbonate azetrope, having about 60 to 70% methanol, and boiling at 63° C. In order to minimize the problem of these azeotropes, it has been found that one of the feeds to the reaction mixture can be a mixture of the alkanol and the dialkyl carbonate which, after processing in the same manner and under the same conditions as shown and described for equation (I), results in the generation of additional dialkyl carbonate which is then recovered from the reaction mixture, the azeotropic mixture being recycled for further processing.

For comparison purposes, comparative Examples 1 through 3 were performed in accordance with the procedure (particularly Example 1 of the patent) set forth in Gaenzler et al., U.S. Pat. No. 3,952,045, previously referred to. The reactions were carried out, in accordance with the patent, employing methanol, carbon monoxide, and oxygen in the presence of a catalyst comprising cupric chloride, an organophosphorus compound, and a cerium compound (ceric sulfate). The reactions were carried out under a pressure of 60 to 100 atmospheres and at a temperature of 150° to 200° C. for one to two hours. Typical results are shown below in Table 1:

TABLE 1

Conversion of Methanol to Dimethyl Carbonate (DMC)

| Comparative Example No. | Catalyst (Gram Weight Ratio = 2/3/2) | Pressure psig | Temperature °C. | Time (hr) | % Conversion |
| --- | --- | --- | --- | --- | --- |
| *1 | $CuCl_2/\phi_3PO/Ce(SO_4)_2$ | 900 | 150 | 2 | 11.5 |
| 2 | $CuCl_2/\phi_3PO/Ce(SO_4)_2$ | 1200 | 170 | 1 | 7.5 |
| 3 | $CuCl_2/\phi_3PO/Ce(SO_4)_2$ | 1500 | 200 | 1 | 8.0 |

*Example 1 of Gaenzler et al patent, 277 grams methanol were used and the volume ratio of oxygen to CO was about 1:2.

The Gaenzler et al. patent does not refer to the by-products produced, but it was found that significant quantities of dimethyl formal, $(CH_3O)_2CH_2$, were produced. The amount of dimethyl formal produced did not appear to be temperature dependent, but there was an increase of the material over the course of time, 18.4% being produced after one hour. In addition, there were traces (less than 1%) of methyl formate.

The catalyst mixture employed in comparative Examples 1 through 3 was not stable to the reaction conditions. There was extensive hydrolysis of the ceric sulfate during the course of the reaction, resulting in a voluminous precipitate of ceric oxide.

Comparative examples were performed omitting the ceric sulfate and the triphenylphosphine oxide of Gaenzler et al in accordance with our invention with the results shown in Table 2. There was less production of dimethyl formal when the cerium salt was omitted, and the results of these examples are shown below in comparative Examples 4 through 6, set forth in Table 2:

TABLE 2

Effect of $Ce(SO_4)_2$ and $\phi_3PO$

| Comparative Example No. | Catalyst | % $DMC^1$ | % Dimethyl Formal |
| --- | --- | --- | --- |
| 4 | $CuCl_2/\phi_3PO/Ce(SO_4)_2$ | 7.8 | 17.9 |
| 5 | $CuCl_2$ | 16.8 | 5.9 |

[1]Conversions after 30 min. at 180° C., 1200 psig, to dimethyl carbonate (DMC)

It was entirely unexpected and in no way could have been predicted that the use of cupric halide would operate as efficiently as it did since attempts to use a cuprous halide such as cuprous chloride gave only a marginal advantage over Gaenzler et al. The yield of dimethyl carbonate using other cupric salts, such as cupric nitrate and cupric sulfate gave only a trace yield of the dimethyl carbonate, when used with methanol and carbon monoxide in the manner executed in accordance with our invention.

Thus, as can be seen from the above examples, the ceric sulfate and the triphenylphosphine oxide appear to promote side reactions and retard reaction rates.

In the following examples employing the copper salts of our invention as catalyst for production of dialkyl carbonates, the reactants employed included anhydrous methanol, dimethyl carbonate, and cupric chloride. The analyses of the reaction products were performed using a 6'×⅛" Porpak QS column installed in a Hewlett-Packard 5754B Gas Chromatograph interfaced to a Spectra-Physics SP4000 Integrator for data reduction. The identity of the gas chromatograph peaks was confirmed by gas chromatography-mass spectrometry. In the various examples listed below, unless otherwise indicated, the equipment employed was a 1-liter Hastelloy-C Magnedrive Autoclave equipped with an internal water cooled coil, an external heating jacket, and a stirring apparatus. In those examples where anhydrous methanol was reacted with carbon monoxide and oxygen, an amount of 277 g (8.66 mols) of anhydrous methanol and 1.00 g (7.5 mmols) of cupric chloride was added. The vessel was sealed and charged to the desired pressure with carbon monoxide and oxygen, the pressure of the carbon monoxide being twice that of the oxygen. The mixture was stirred at a rate of 500 rpm, and then warmed to 175° C. Reaction began at this point, and the temperature rose rapidly, but was maintained with periodic cooling at 175°-185° C. Carbon monoxide and oxygen were added periodically to maintain the pressure. After about 10 minutes, cooling was halted and the mixture was maintained at 180° C.±5° C. for a total of 30 minutes, and then cooled to room temperature.

Employing the carbonylation techniques, with the equipment and reactants as set forth above, the following results were obtained:

TABLE 3
Conversion of Methanol to Dimethyl Carbonate

| Example No. | Mole % Cupric Chloride × 10⁶ | Pressure (psig) | T (°C.) | Time (hours) | % Conversion to DMC |
|---|---|---|---|---|---|
| 6 | 867 | 2500 | 180 | 0.5 | 15.0 |
| 7 | 867 | 1500 | 180 | 0.5 | 14.6 |
| 8 | 867 | 600 | 180 | 0.5 | 14.0 |
| 9 | 867 | 1500 | 160 | 0.5 | No reaction |
| 10 | 867 | 1500 | 180 | 0.5 | 14.7 |
| 11 | ᵃ220 | 1500 | 180 | 0.5 | 6 |
| 12 | 867 | 1500 | 180 | 0.5 | 14.5 |
| 13 | 1155 | 1500 | 180 | 0.5 | 11.4 |
| 14 | 867 | 1500 | 180 | 0.25 | 12.0 |
| 15 | 867 | 1500 | 180 | 1.0 | 17.9 |
| 16 | 867 | 1500 | 180 | 2.0 | 20.0 |

ᵃReaction time too short for catalyst concentration used

Little effect on reaction rate, byproduct production, and percent conversion was noticed based upon changes in pressure. The reaction proceeded well at 600 psig, and equivalent results were obtained at higher pressures. In each case, because of the consumption of carbon monoxide and oxygen, in essentially the 2:1 molar ratio in which they were introduced, carbon monoxide and oxygen had to be added continually to maintain the desired pressures within ±75 psi.

As indicated previously, the reaction does not proceed until a temperature of above 160° C. is reached. Reaction is rapid, however, at 180° C. The desired temperature range is maintained by the cooling equipment provided on the reaction vessel since the reactions were extremely exothermic.

EXAMPLE 17

As indicated, the process of the present invention can also be carried out employing azeotropic mixtures of methanol and dimethyl carbonate, rather than methanol alone. The equipment described above for Examples 1 through 16 was employed here and was charged with 180 g (5.621 mols) of methanol, 120 g (1.331 mols) of dimethyl carbonate and 1.0 g (0.0075 mol) of cupric chloride. The mixture was pressurized with 1000 psig of carbon monoxide and 500 psig of oxygen. It was warmed to 180° C. for 30 minutes. Upon cooling, gas chromatography indicated the presence of 176.3 g (1.96 mols) of dimethyl carbonate. This was an increase of 56.3 g (22%) of the dimethyl carbonate.

The reaction mixture from Example 17 was transferred to 500 ml round bottom flask equipped with a 12-inch vacuum jacketed distilling column packed with glass helices and a pressure equalizing take-off head. Material was removed at a head temperature of 63° C. to collect 230 g of the methanoldimethyl carbonate azeotrope. When the pot residue was cooled to 25° C., it separated into an aqueous phase containing the cupric chloride and dimethyl carbonate phase. The dimethyl carbonate phase was separated, and a water-dimethyl carbonate azeotrope was removed at 78° C. The distillate underwent phase separation and the lower dimethyl carbonate layer was returned to the pot. A small forecut, approximating 0.3 g, was removed and pure dimethyl carbonate was then distilled at 91° C. to obtain 80.0 g of dimethyl carbonate, a yield of 96%. The material was pure according to gas chromatography. The remaining aqueous phase was evaporated to dryness to obtain 0.92 g (92%) of cupric chloride.

EXAMPLE 18

The catalyst recovered in Example 17 was reused in a reaction of the type described for Example 17 employing 180 g (5.62 mols) of methanol and 120 g (1.33 mols) of dimethyl carbonate. Reaction was carried out at 180° C. for 30 minutes and resulted in 178.2 g (1.98 mols) of dimethyl carbonate, an increase of 58.2 grams of dimethyl carbonate for a total yield of 22%, a result almost identical to that obtained in Example 17.

EXAMPLE 19

A quantity of 300 grams ethanol was reacted at 180° C. employing 1000 psi carbon monoxide pressure and 500 psi oxygen pressure in the same equipment as described for Example 17 and with other conditions being equivalent. The resulting diethyl carbonate was obtained in a yield of about 8.2% after 30 minutes reaction time.

Other alkanols, including isopropanol, propanol, and butanols can be reacted with carbon monoxide and oxygen, employing conditions similar to those set forth here, with similar results, except for somewhat lower yields. Similarly, results equivalent to those shown above can be obtained, using other cupric halide catalysts, e.g., cupric bromide, etc.

Thus, it has been shown that dialkyl carbonates can be prepared in high yield from the corresponding alkanols, carbon monoxide, and oxygen employing a cupric halide catalyst. The water, which is coproduced in the reaction, does not poison the catalyst, so that the catalyst can be recovered and recycled for further processing of the alkanol materials to the dialkyl carbonates. To minimize the problems generated by the production of an azeotrope of the alkanol and the dialkyl carbonate, where appropriate, the azeotropic mixture could be carbonylated, the dialkyl carbonate recovered and the azeotrope recycled for further processing.

While specific examples of the invention have been shown and described, the invention should not be considered as so limited, but only as limited by the appended claims.

What we claim as new and desire to secure by Letters Patent of the United States is:

1. A process for the production of dialkyl carbonate from alkanols in accordance with the following reaction:

$$4ROH + 2CO + O_2 \xrightarrow{\text{Cupric Halide}} 2R_2CO_3 + 2H_2O$$

where R is selected from the class consisting of methyl, ethyl, propyl, isopropyl, and butyls, comprising reacting the alkanol, carbon monoxide, and oxygen at a temperature above 170° C. and at elevated pressures in the presence of from 0.02 to 1.5%, by weight, cupric halide catalyst, based on the weight of the alkanol.

2. The process of claim 1 wherein the copper catalyst is selected from the class consisting of cupric chloride and cupric bromide.

3. The process of claim 1 wherein the reaction temperature is from 180° to 300° C.

4. The process of claim 1 wherein R is methyl.

5. The process of claim 1 wherein the copper catalyst is recovered from the reaction mixture and is recycled.

6. A process for preparing dimethyl carbonate, comprising reacting, at a temperature about 170° C. and at elevated pressures in the presence of a cupric halide catalyst, an azeotropic mixture of dimethyl carbonate and methanol with carbon monoxide and oxygen.

7. The process of claim 6 wherein the cupric catalyst is selected from the class consisting of cupric chloride and cupric bromide.

8. The process of claim 7 wherein the reaction temperature is from 180° to 300° C.

9. The process of claim 7 wherein the cupric halide catalyst is recovered from the reaction mixture and is recycled.

* * * * *